US006265448B1

(12) United States Patent
Steiner et al.

(10) Patent No.: US 6,265,448 B1
(45) Date of Patent: Jul. 24, 2001

(54) METHOD FOR CHEMOPREVENTION OF PROSTATE CANCER

(75) Inventors: Mitchell S. Steiner; Sharon Raghow, both of Germantown, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/306,958

(22) Filed: May 7, 1999

Related U.S. Application Data

(60) Provisional application No. 60/084,602, filed on May 7, 1998.

(51) Int. Cl.[7] .................................................. A61K 31/135
(52) U.S. Cl. .......................................... 514/648; 514/651
(58) Field of Search ...................................... 514/648, 651

(56) References Cited

U.S. PATENT DOCUMENTS

| 4,329,364 | 5/1982 | Neri et al. . |
| 4,474,813 | 10/1984 | Neri et al. . |
| 4,696,949 | 9/1987 | Toivola et al. . |
| 4,990,538 | 2/1991 | Harris et al. . |
| 5,491,173 | 2/1996 | Toivola et al. . |
| 5,571,534 | 11/1996 | Jalonen et al. . |
| 5,595,722 | 1/1997 | Grainger et al. . |
| 5,595,985 | 1/1997 | Labrie . |
| 5,599,844 | 2/1997 | Grainger et al. . |
| 5,605,700 | 2/1997 | DeGregorio et al. . |
| 5,629,007 | 5/1997 | Audia et al. . |
| 5,635,197 | 6/1997 | Audia et al. . |
| 5,650,425 | 7/1997 | Biegnon et al. . |
| 5,788,964 | 8/1998 | Baral et al. . |

FOREIGN PATENT DOCUMENTS

| 095875 | 12/1983 | (EP) . |
| 415 623 A2 | 3/1991 | (EP) . |
| 616 529 B1 | 9/1994 | (EP) . |
| WO 94/12162 | 6/1994 | (WO) . |
| WO 95/26720 | 10/1995 | (WO) . |
| 98/58634 | 12/1998 | (WO) . |
| WO 98/58634 | 12/1998 | (WO) . |

OTHER PUBLICATIONS

Bergan RC et al. "A Phase III Study Of High–Dose Tamoxifen In Patients With Hormone–Refractory Prostate Cancer." Clin Cancer Res 1999 Sep.; 5(9): 2366–73.
Chang William Y et al. "Estrogen Receptor–β; Implications For The Prostate Gland" The Prostate 40:115–124 (1999).
Shughrue Paul J. et al. "Comparative Distribution Of Estrogen Receptor–α (Er–α) And β (Er–β) mRNA In The Rat Pituitary, Gonad, And Reproductive Tract" Steroids 63: 498–504, 1998, Elsevier Science Inc.
Prins Gail S. et al, "Neonatal Estrogen Exposure Up–Regulates Estrogen Receptor Expression In The Developing And Adult Rat Prostate Lobes*", Endocrinology 138: 1801–1809, 1997).
Hempstock J. et al. "Growth Inhibition Of Prostate Cell Lines In Vitro By Phyto–Oestrogens", British Journal Of Urology (1998). 82, 560–563.
Awoniyi Caleb A. et al. "Neonatal Exposure To Coumestrol, A Phystoestrogen, Does Not Alter Spermatogenic Potential In Rats", Endocrine, vol. 7, No. 3, 337–341, Dec. 1997.
"Chemoprevention Of Prostate Cancer: Guidelines For Possible Intervention Strategies", Journal of Cellular Biochemistry, Supplement 16H:140–145 (1992).
"When Is Intervention Warranted?", Journal Of Cellular Biochemistry, Supplement 16H:138–139 (1992).
"Editorial: A New Actor In The Estrogen Receptor Drama–Entre ER–β", Endocrinology vol. 138, No. 3, (1997).
Kuiper George G. J. M. et al. "Comparison Of The Ligand Binding Specificity And Transcript Tissue Distribution Of Estrogen Receptors α and β", Endocrinology vol. 138, No. 3, 863–870 (1997).
Colletta Anthony A. et al. "Alternative Mechanisms Of Action Of Anti–Oestrogens" Breast Cancer Research and Treatment 31: 5–9, 1994.
Bonkhoff H et al. "Estrogen Receptor Expression In Prostate Cancer and Premalignant Prosatic Lesions", American Journal of Paibology, vol. 155, No. 3 Aug. 1999.
Xiaolin Zi et al. Silibinin Decreases Prostate–Specific Antigen With Cell Growth Inhibition Via G1 Arrest, Leading To Differentiation Of Prostate Carcinoma Cells: Implications For Prostate Cancer Intervention:, Proc. Nsil. Acad. Sci, USA vol. 96, pp. 7490–7495, Jun. 1999, Medical Sciences.
Landstrom M, et al. Inhibitory Effects Of Soy and Rye Diets On The Development Of Dunning R3327 Prostate Adenocarcinoma in Rats, The Prostate 36: 151–161 (1998).
Buelke–Sam J. et al. "The Selective Estrogen Receptor Modulator, Raloxifene: An Overview Of NonClinical Pharmacology And Reproductive And Developmental Testing", Reprod Toxicol 1998 May–Jun.; 12(3):217–21.

(List continued on next page.)

Primary Examiner—Jerome D. Goldberg
(74) Attorney, Agent, or Firm—Eitan, Pearl, Latzer & Cohen-Zedek; Mark S. Cohen (57) ABSTRACT

This invention provides the chemoprevention of prostate cancer and, more particularly, to a method of administering to a subject an effective dose of a chemopreventive agent, toremifene and analogs or metabolites thereof, to prevent recurrence of, suppress or inhibit prostate carcinogenesis.

The present invention provides a safe and effective method for suppressing or inhibiting latent prostate cancer and is particularly useful for treating subjects having an elevated risk of developing prostate cancer, for example, those having benign prostatic hyperplasia, prostate intraepithelial neoplasia (PIN), or an abnormally high level of circulating prostate specific antibody (PSA), or who have a family history of prostate cancer.

19 Claims, 6 Drawing Sheets

(3 of 6 Drawing Sheet(s) Filed in Color)

OTHER PUBLICATIONS

Treinen KA et al. An Evaluation Of The Novel Selective Estrogen Receptor Modulator, Idoxifene, For Effects On Reproduction In Rats And Rabbits:, Toxicol Sci 1998 Feb.; 41(2):199–207.

Boehm S et al. "Estrogen Suppression As A Pharmacotherapeutic Strategy In The Medical Treatment Of Benign Prostatic Hyperplasia: Evidence For Its Efficacy From Studies With Mepartricin" Wien Klin Wochenschr Dec. 11, 1998; 110(23):817–23.

Dhar JD et al. "Estrogen, Androgen and Antiestrogen Responses In The Accessory Organs Of Male Rats During Different Phases Of Life", Endocr Res 1998 May; 24(2): 159–69.

West Neal B et al. "Estrogen and Progestin Receptors And Aromatase Activity In Rhesus Monkey Prostate" Endocrinology , vol. 1. 123, (1998).

Strauss L "Genistein Exerts Estrogen–Like Effects In Male Mouse Reproductive Tract", Molecular and Cellular Endocrinology 144 (1998)83–93, Elsevier Science Ireland Ltd.

Strom Sara S. et al. "Phytoestrogen Intake and Prostate Cancer: A Case–Control Study Using A New Database", Nutrition and Cancer, 33(1), 20–25. (1999).

Kellof GJ et al.. "Strategies For Chemoprevention Of Prostate Cancer", Prostate Cancer and Prostate Disease (1988) 5. 107.

Buelke–Sam Judy et al. "The Selective Estrogen Receptor Modulator, Raloxifene: An Overview OfNonClinical Pharmacology and Reproductive Development Testing", Reproductive Toxicology vol. 12, No. 3 pp. 217–221, 1998.

Hobisch Alfred "Metastatic Lesions From Prostate Cancer Do Not Express Oestrogen And Progesterone Receptors" J. Pathol. 182: 356–361, 1997.

Albert David S. et al. "An Overview Of Clinical Cancer Chemoprevention Studies With Emphasis On Positive Phase III Studies" Overivew of Diet Cancer 6928–6975 (1995).

Prins Gail S. "Developmental Estrogenization Of The Prostate Gland", Prostate:Basic and Clinical Aspects p. 245–263 (1997).

Kuiper George G. J. M. "Cloning Of A Novel Estrogen Receptor Expressed In Rat Prostate And Ovary", Proc. Natl. Acad. Sci USA vol. 93, pp. 5925–5930, Jun. 1996 Biochemistry.

Kuiper George G. J. M. "Interaction Of Estrogenic Chemicals and Phytoestrogens With Estrogen Receptor β", Endocrinology vol. 139, No. 10 (1998).

Horton John et al. "Tamoxifen In Advanced Prostate Cancer An BCOG Pilot Study", The Prostate 12: 173–177 (1988).

Martin R. Schneider et al. "Nonsteroidal Antiestrogens and Partial Estrogens with Prostatic Tumor Inhibiting Activity", Cancer Research Clinical Oncology Springer–Verlag 1986, J Cancer Res Clin Oncol (1986) 112: 258–265, p. 258–265.

Celine Martel et al. "Binding Characteristics of Novel Nonsteroidal Antestrogens to the Rat Uterine Estrogen Receptors", Pergamon, J. Steroid Biochem. Molec. Bio.., vol. 64, No. 3–4, pp. 199–205, 1998.

Richard Gams, MD "Phase III Trials of Toremifene vs Tamoxifen" Oncology vol. 11, No. 5, Supplement 4, May 1997.

Christian Rohlff et al. "Prostate Cancer Cell Growth Inhibition by Tamoxifen Is Associated With Inhibition of Protein linase C and Induction of p21" The Prostate 37:51–59 (1998) ©1998 Wiley–Liss, Inc.

Greenwald "Expanding Horizons in Breast and Prostate Cancer Prevention and Early Detection", in J. Cancer Education, 1993, vol. 8, No. 2, pp. 91–107.

Brawley et al., "Chemoprevention of Prostate Cancer" in Urology, 1994, vol. 43, No. 5.

Kelloff et al., "Introductory Remarks: Development of Chemopreventive Agents for Prostate Cancer" in Journal of Cellular Biochemistry, 1992, Supplement 16H: 1–8.

Lucia et al., "Chemopreventive Activity of Tamoxifen, N–(4–Hydroxyphenyl)retinamide, and the Vitamin D Analogue Ro24–553 1 for Androgen–promoted Carcinomas of the Rat Seminal Vesicle and Prostate" in Cancer Research, 1995, vol. 55, pp. 5621–5627.

Potter et al., "A Mechanistic Hypothesis for DNA Adduct Formation By Tamoxifen Following Hepatic Oxidative Metabolism" in Carcinogenesis, 1994, vol. 15, No. 3, pp. 439–442.

Gingrich et al., "Androgen–independent Prostate Cancer Progression in the Tramp Model", in Cancer Research 57, Nov. 1, 1997, pp. 4687–4691.

Gingrich et al., "Pathologic Progression of Autochthonous Prostate Cancer in the Tramp Model", Prostate Cancer and Prostatic Diseases, 1999, 2, pp. 70–75.

Gingrich et al., "Metastatic Prostrate Cancer in a Transgenic Mouse", in Cancer Research 56, Sep. 15, 1996, pp. 4096–4102.

Gershanovich et al., "A Phase III Comparison of Two Toremifene Doses to Tamoxifen in Postmenopausal Women with Advanced Breast Cancer", Breast Cancer Research and Treatment 45, 1997, pp. 251–262.

Pyrhönen et al., "Comparison of Toremifene and Tamoxifen in Postmenopausal Patients with Advanced Breast Cancer: a Randomized Double–blind, the 'Nordic' Phase III Study", British Journal of Cancer, 1997, 76(2), pp. 270–277.

Neubauer et al., "Endocrine and Antiprostatic Effects of Raloxifene (LY156758) in the Male Rat", The Prostate 23, 1993, pp. 245–262.

Pollard, "Prevention of Prostate–Related Cancers in Lobund–Wistar Rats", The Prostate 39, 1999, pp. 305–309.

Simard et al., "Keoxifene Shows Pure Antiestrogenic Activity in Pituitary Gonadotrophs", Molecular and Cellular Endocrinology 39, 1985, pp. 141–144.

Hietanen T "Open Phase II Study of High–Dose Toremifene as First–Line Therapy for Advanced Breast Cancer" in Oncology—May 1997; 11(5 Suppl 4): 37–40.

Hayes "A Randomized Comparison of Tamoxifen (TAM) and Two Separate Doses of Toremifene (TOR) in Postmenopausal Patients with Metastatic Breast Cancer (MBC) (Meeting Abstract)" in Proc Annu Met Am Soc Clin Oncol; 14:A71 1995.

Black et al. "Uterine Bioassay of Tamoxifen, Trioxifene and a New Estrogen Antagonist (LY117018) in Rats and Mice" in Life Sciences, 1980, vol. 26, pp. 1453–1458.

Moore et al. "Regulation of Cytoplasmic Dihydrotestosterone Binding in Dog Prostate by 17β–Estadiol", in J. Clin. Invest. © The American Society for Clinical Investigation, Inc., vol. 63 Mar. 1979, pp. 351–357.

Shirai et al. "Effects of Testosterone, Dihydrotestosterone and Estrogen on 3.2'–Dimethyl–4–Aminobiphenyl–Induced Rat Prostate Carcinogenesis" in Int. J Cancer: 57, 224–228 (1994).

Greenwald et al. "Breast Cancer Prevention and Early Detection", pp. 93–106.

Shenfeld et al. "Androgen Deprivation Therapy", Chapter 37, Section III/Prostate Cancer, pp. 467–477.

Jordan VC "Toremifene As An Anticancer Agent", Cancer Invest 1990; 8(2)271.

Karlsson S. et al. "A Two–Year Dietary Carcinogenicity Study Of The Antiestrogen Toremifene In Sprague–Dawley Rats" Drug Chem Toxicol Nov. 1996; 19(4): 245–66.

Powles TJ "Status Of Antiestrogen Breast Cancer Prevention Trials" Oncology (Huntingt) Mar. 1998; 12(3 Suppl 5): 28–31.

Moon RC et al. "Chemoprevention of MNU–Induced Mammary Tumorigenesis by Hormone Response Modifiers: Toremifene, RU 16117, Tamoxifen, Aminoglutethimide Progesterone", Anticancer Res May–Jun. 1994; 14(3A): 889–93.

Nevalainen MT et al. "Expression and Hormone Regulation Of Prolactin Receptors in Rat Dorsal and Lateral Prostate", Endocrinology Jul. 1996; 137(7): 3078–88.

Foekens JA et al. "Expression Of Prostate–Specific Antigen (PSA) Correlates With Poor Response To Tamoxifen Therapy In Recurrent Breast Cancer", Br J Cancer Feb. 1999; 79(5–6): 888–94.

Brandes LJ et al. "Salutary Clinical Response Of Prostate Cancer To Antiandrogen Withdrawal: Assessment Of Flutamide In An In Vitro Paragdigm Predictive Of Tumor Growth Enhancement", Clin Cancer Res Aug. 1997; 3(8): 1357–61.

Miyata E et al. "Effects Of Tamoxifen, An Antiestrogen, On Rat Prostate Carcinogenesis by 3,2'–Dimethyl–4–Aminobiphenyl And Testerone Do Not Support An Estrogen Role In Testerone Promotion", Prostate Apr. 1, 1997;31(1)9–13.

Pienta KJ et al. "A Phase II Evaluation Of Oral Tamoxifen And Intermittent Intravenous Vinblastine In Hormone–Refractory Adenocarcinoma Of The Prostate"., Am J Clin Oncol Oct. 1996; 19(5):500–3.

Pienta KJ et al. "Inhibition Of Prostate Cancer Growth By Vinblastine And Tamoxifen", Prostate May 1995; 26(5): 270–4.

Lippman SM et al. "Cancer Chemoprevention", J Clin Oncol Apr. 1994; 12(4):851–73.

Szarka CE et al. "Chemoprevention Of Cancer", Curr Probl Cancer Jan.–Feb. 1994; 18(1):6–79.

Yu H et al. "Induction Of Prostate Specific Antigen Production By Steroids And Taxoxifen In Breast Cancer Cell Lines", Breast Cancer Res Treat 1994; 32(3)291–300.

Horton J et al. "Tamoxifen In Advanced Prostate Cancer: An ECOG Pilot Study", Prostate 1988; 12(2):173–7.

Kangas L "Development And Biochemical Pharmacology Of Toremifene, An Antiestrogenic Antitumor Drug", Acta Obstet Gynecol Scand 1991; 70(4–5): 399.

Anttila M et al. "Pharmacokinetics Of The Novel Antiestrogenic Agent Toremifene In Subjects With Altered Liver And Kidney Function" Clin Pharmacol Ther Jun. 1995; 57(6):628–35.

Kamat AM et al. "Chemoprevention Of Urological Cancer", The Journal Of Urology, vol. 161. 1748–1760. Jun. 1999, p. 1748–1760.

Fleton SA "Potential New Antiestrogens For The Treatment Of Breast Cancer", Highlights in Oncology Practice vol. 15, No. 2, 1997 p. 47–52.

Nevalainen M.T. et al. "Estrogen and Prolactin Regulation of Rat Dorsal and Lateral Prostate in Organ Culture", Endocrinology, vol. 129, No. 2 pp. 612–618.

Price K. R. et al. "Naturally Occurring Oestrogens in Food—A review", Food Additives and Contaminants, 1985, vol. 2, No. 2, 73–106.

Nevalanine et al. "Hormone Regulation of Human Prostate in Organ Culture" Cancer Ress, vol. 53, No. 21, 1993, pp. 519–5207, XPOO2117653.

Bostwick, Seminars in Urologic Oncology, vol. 17, No. 4, pp. 187–198, Nov. 1999.*

* cited by examiner

| TIME AFTER TREATMENT | % CHANGE RELATIVE TO DAY 0 |
|---|---|
| WEEK 3 (n=11) | 9.44 |
| WEEK 4 (n=8) | 115.27 |
| WEEK 5 (n=8) | 271.71 |
| WEEK 6 (n=8) | 600.88 |

| TIME AFTER TREATMENT | % CHANGE RELATIVE TO DAY 0 |
|---|---|
| WEEK 3 (n=12) | −34.58 |
| WEEK 4 (n=8) | −61.01 |
| WEEK 5 (n=8) | −74.51 |
| WEEK 6 (n=6) | −61.72 |

FIG.6

METHOD FOR CHEMOPREVENTION OF PROSTATE CANCER

This application claim benefit to Provisional Application No. 60/084,602 filed May 7, 1998.

FIELD OF INVENTION

This invention relates to the chemoprevention of prostate cancer and, more articularly, to a method of administering to a subject an effective dose of an gent to prevent the recurrence of, suppression or inhibition of prostate arcinogenesis.

BACKGROUND OF THE INVENTION

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients. Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of chemoprevention strategies against prostate cancer may have the greatest overall impact both medically and economically against prostate cancer.

Because of the high incidence and mortality of prostate cancer, it is imperative to develop chemoprevention strategies against this devastating disease. Understanding those factors that contribute to prostate carcinogenesis including the initiation, promotion, and progression of prostate cancer will provide molecular mechanistic clues as to appropriate points of intervention to prevent or halt the carcinogenic process. New innovative approaches are urgently 5 needed at both the basic science and clinical levels to decrease the incidence of prostate cancer as well as to halt or cause the regression of latent prostate cancer. As the frequency of prostate cancer escalates dramatically at the same ages when men are confronted by other competing causes of mortality, simply slowing the progression of prostate adenocarcinoma may be both a more 10 suitable and cost effective health strategy.

Various approaches have been taken to the chemoprevention of prostate cancer. Greenwald, "Expanding Horizons in Breast and Prostate Cancer Prevention and Early Detection" in J. Cancer Education, 1993, Vol. 8, No. 2, pages 91-1 07, discusses the testing of 5α-reductase inhibitors such as finasteride for the prevention of prostate cancer Brawley et al., "Chemoprevention of Prostate Cancer" in Urology, 1994, Vol. 43, No. 5, also mentions 5α-reductase inhibitors as well as difluoromethylornithine and retinoids as potential chemopreventive agents.

Kelloff et al., "Introductory Remarks: Development of Chemopreventive Agents for Prostate Cancer" in Journal of Cellular Biochemistrv, 1992, Supplement 16H: 1–8, describes National Cancer Institute preclinical studies of seven agents: all-trans-N-(4-hydroxyphenyl)retinamide, difluoromethylornithine, 25 dehydroepiandrosterone, liarozole, lovestatin, oltipraz, and finasteride.

Lucia et al., "Chemopreventive Activity of Tamoxifen, N-(4-Hydroxyphenyl)retinamide, and the Vitamin D Analogue Ro24-553 1 for Androgen-promoted Carcinomas of the Rat Seminal Vesicle and Prostate" in 30 Cancer Research, 1995, Vol.55, pages 5621–5627, reports chemoprevention of prostate carcinomas in Lobund-Wistar rats by tamoxifen, an estrogen response modifier. As discussed in Potter et al., "A mechanistic hypothesis for DNA adduct formation by tamoxifen following hepatic oxidative metabolism" in Carcinogenesis, 1994, Vol. 15, No. 3, pages 439–442, tamoxifen causes liver carcinogenicity in rats, which is attributed to the formation of covalent DNA 5 adducts. This reference also reports that the tamoxifen analogue toremifene, which showed a much lower level of hepatic DNA adduct formation than tamoxifen, is non-carcinogenic.

Toremifene is an example of a triphenylalkene compound described in U.S. Pat. Nos. 4,696,949 and 5,491,173 to Toivola et al., the disclosures of which are incorporated herein by reference. The parenteral and topical administration to mammalian subjects of formulations containing toremifene are described in U.S. Pat. No. 5,571,534 to Jalonen et al. and in U.S. Pat. No. 5,605,700 to DeGregonio et al., the disclosures of which are incorporated herein by reference.

Toremifene-containing formulations for reversing the multidrug resistance to cancer cells to a cytotoxic drug are described in U.S. Pat. No. 4,990,538 to Harris et al., the disclosure of which is incorporated herein by reference. U.S. Pat. Nos. 5,595,722 and 5,599,844 to Grainger et al., the disclosures of which are incorporated herein by reference, describe methods for identifying agents that increase TGFP levels and for orally administering formulations containing TGFP activators and TGFP production stimulators to prevent or treat conditions characterized by abnormal proliferation of smooth muscle cells, for example, vascular trauma. Disclosed agents for increasing TGFP levels include tamoxifen and its analogue toremifene.

U.S. Pat. Nos. 5,629,007 and 5,635,197 to Audia et al., the disclosures of which are incorporated herein by reference, describe a method of preventing the development of prostatic cancer at risk of developing such cancer, for example, 30 a patient having benign prostatic hyperplasia, by administering to the patient an octahydrobenzo[fJquinolin-3-one compound.

U.S. Pat. No. 5,595,985 to Labrie, the disclosure of which is incorporated herein by reference, also describe a method for treating benign prostatic hyperplasia using a combination of a 5α-reductase inhibitor and a compound that binds and blocks access to androgen receptors. One example of a compound that blocks androgen receptors is flutamide.

U.S. Pat. Nos. 4,329,364 and 4,474,813 to Neri et al., the disclosures of which are incorporated herein by reference, describe pharmaceutical preparations comprising flutamide for delaying and/or preventing the onset of prostate carcinoma. The preparation can be in the form of a capsule, tablet, suppository, or elixir. Despite these developments, there is a continuing need for agents and methods effective for preventing prostate cancer. The present invention is directed to satisfying this need.

SUMMARY OF THE INVENTION

This invention provides the chemoprevention of prostate cancer and, more particularly, to a method of administering to a subject an effective dose of a chemopreventive agent, toremifene and analogs or metabolites thereof, to prevent recurrence of, treatment, suppression or inhibition of prostate carcinogenesis.

The present invention is directed to a method for preventing prostate carcinogenesis. This invention involves administering to a mammalian subjeit a pharmaceutical preparation of a chemopreventive agent having the formula:

(1)

wherein $R_1$ and $R_2$, which can be the same or different, are H or OH, $R_3$ is $OCH_2CH_2NR_4R_5$, wherein $R_4$ and $R_5$, which can be the same or different, are H or an alkyl group of I to about 4 carbon atoms;

and their pharmaceutically acceptable carrier, diluents, salts, esters, or N-oxides, and mixtures thereof.

The present invention provides a safe and effective method for suppressing or inhibiting latent prostate cancer and is particularly useful for treating subjects having an elevated risk of developing prostate cancer, for example, those having benign prostatic hyperplasia, prostate intraepithelial neoplasia (PIN), or an abnormally high level of circulating prostate specific antibody (PSA), or who have a family history of prostate cancer.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 6A$14 6B: Comparison of placebo vs. Toremifene effects on tumor growth.

DETAILED DESCRIPTION OF THE INVENTION

This invention provides a method for preventing prostate carcinogenesis; 2) methods for suppressing or inhibiting prostate cancer; 3) methods for reducing the risk of developing prostate cancer; and 4) methods for increasing the survival rate of a subject using the prostate chemopreventive agent, toremifene, analogs and metabolites thereof.

As demonstrated herein, Toremifene is a prostate chemopreventive agent. In the 10 experiments conducted herein, the prostates were actually dissected and evaluated both histologically and by wholemount analysis. Also, Toremifene was tested for the treatment of prostate cancer by treating LNCaP xenografts in nude mice. As is shown, the data is quite dramatic, not only has Toremifine inhibited growth, but actually Toremifene was able to produce regression of the tumors,

The present invention is directed to a method for preventing prostate carcinogenesis. This invention involves administering to a mammalian subject a pharmaceutical preparation of a chemopreventive agent having the formula:

(1)

wherein $R_1$ and $R_2$, which can be the same or different, are H or OH, $R_3$ is $OCH_2CH_2NR_4R_5$, wherein $R_4$ and $R_5$, which can be the same or different, are H 30 or an alkyl group of 1 to about 4 carbon atoms; and their pharmaceutically acceptable carrier, diluents, salts, esters, or N-oxides, and mixtures thereof.

This invention provides for the use of a pharmaceutical composition for reventing the recurrence of, suppressing or inhibiting prostate carcinogenesis, or increasing the survival rate of a subject having prostate cancer, comprising chemopreventive agent having the formula:

(1)

wherein $R_1$ and $R_2$, which can be the same or different, are H or OH, $R_3$ is $OCH_2CH_2NR_4R_5$, wherein $R_4$ and $R_5$, which can be the same or different, are H or an alkyl group of 1 to about 4 carbon atoms; and their pharmaceutically acceptable carrier, diluents, salts, esters, or N-oxides, and mixtures thereof.

The present invention provides a safe and effective method for suppressing or inhibiting latent prostate cancer and is particularly useful for treating subjects having an elevated risk of developing prostate cancer, for example, those having benign prostatic hyperplasia, prostate intraepithelial neoplasia (PIN), or an abnormally high level of circulating prostate specific antibody (PSA), or who have a family history of prostate cancer.

The compound 4-chloro-1,2-diphenyl-1-[4-[2-(N,N-dimethylamino) ethoxy]phenyl]-1-butene of formula (I), where $R_1$ and $R_2$ are each H and $R_4$ and $R_5$ are each methyl, is named toremifene. Toremifene has been shown safe and effective as an anti-tumor compound and exhibits hormonal effects as an estrogenic or as an anti-estrogenic agent, depending on the dosage used. On administration, toremifene has several metabolites that are also biologically active.

This invention also provides for use of toremifene analogs or metabolites thereof, which are well known to those skilled in the art. Other examples of chemopreventive agents of formula (1) are the following: 4-chloro-1,2-diphenyl-1 -[4-[2-(N-methylamino)ethoxy]phenyl]-1-butene; 4-chloro- 1,2-diphenyl4-[4-[2-(N,N-10 diethylamino)ethoxy]phenyl]-1-butene; 4-chloro-1,2-diphenyl-1-14-(aminoethoxy)phenyl]-1-butene; 4-chloro-1-(4-hydroxyphenyl)-1-[4-[2-(N,N-dimethylamino)ethoxy]phenyl]-2-phenyl- 1 -butene; 4-chloro- 1-(4-hydroxyphenyly 1-[4-[2-(N- methylamino)ethoxy]phenyl]-2- phenyl-1 -butene; and 4-chloro-1,2-bis (4hydroxyphenyl)-1-[4-[2-(N,N-dimethylamino) ethoxy]phenyl]-1-butene.

The invention encompasses pure (Z)- and (E)- isomers of the compounds and mixtures thereof as well as pure (RR,SS) and (RS,SR)-enantiomer couples and mixtures thereof.

The agent compounds of formula (I) can be prepared according to procedures described in the previously cited U.S. Pat. Nos. 4,696,949 and 5,491,173 to Toivola et al.

The invention includes pharmaceutically acceptable salts of amino-substituted compounds with organic and inorganic acids, for example, citric acid and hydrochloric acid. The invention also includes N-oxides of the amino substituents of the compounds of formula (1). Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

As used herein, "pharmaceutical composition"means therapeutically effective amounts of the agent together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" are well known to those skilled in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenousvehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, California, p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (*bacille Calmette-Guerin*) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms protective coatings, protease inhibitors or permeation enhancers for various routes of administration, including parenteral, pulmonary, nasal and oral. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half- lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984). Preferably, a controlled release device is introduced into a subject in proximity of the site of inappropriate immune activation or a tumor. Other controlled release systems are discussed in the review by Langer (Science 249:1527–1533 (1990).

The method of the present invention for preventing prostate carcinogenesis involves administering to a mammalian subject a pharmaceutical preparation comprising chemopreventive agent or a metabolite or salt thereof. The pharmaceutical preparation can comprise the chemopreventive agent alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the chemopreventive agent can be administered to a subject by, for example, subcutaneous implantation of a pellet; in a further embodiment, the pellet provides for controlled release of chemopreventive agent over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical preparation can also be a parenteral formulation; in one embodiment, the formulation comprises a liposome that includes a complex of a chemopreventive agent such as, for example, toremifene and a cyclodextrir compound, as described in the previously cited U.S. Pat. No. 5,571,534 to Jalonen et al.

The pharmaceutical preparations of the invention can be prepared by known dissolving, mixing, granulating, or tablet-forming processes. For oral administration, the chemopreventive agents or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the chemopreventive agents or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the chemopreventive agents or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527–1533 (1990); Treat et al., in Liposomes in the Therapy ofinfectious Disease and Cancer, Lopez-Berestein and Fidler (eds.), Liss, NewYork, pp. 353–365 (1989); Lopez-Berestein, ibid., pp. 317–327; see generally ibid).

The pharmaceutical compositions of the present invention are particularly useful for treating a subject having an elevated risk of developing prostate cancer. High-risk subjects include, for example, those having benign prostatic hyperplasia, prostatc intraepithelial neoplasia (PIN), or an abnormally high level of circulating prostate specific antibody (PSA), or who have a family history of prostate cancer.

Further, the prostate chemopreventive agent may be administered in combination with other cytokines or growth factors include but are not limited to: IFN y or α, IFN-β; interleukin (IL) 1, IL-2, IL4, IL-6, IL-7, IL-12, tumor necrosis factor (TNF) α, TNF-β, granulocyte colony stimulating factor (G-CSF), granulocyte/macrophage CSF (GM-CSF); accessory molecules, including members of the integrin superfamily and members of the Ig superfamily such as, but not limited to, LFA-1, LFA-3, CD22, and B7-1, B7-2, and ICAM-1 T cell costimulatory molecules.

The chemopreventive agent may precede or follow a DNA damaging agent treatment by intervals ranging from minutes to weeks. Protocols and methods are known to those skilled in the art. DNA damaging agents or factors are known to those skilled in the art and means any chemical compound or treatment method that induces DNA damage when applied to a cell. Such agents and factors include radiation and waves that induce DNA damage such as, gamma -irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In another embodiment one may irradiate the localized tumor site with DNA damaging radiation such as X-rays, UV-light, gamma -rays or even microwaves. Alternatively the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like.

Other factors that cause DNA damage and have been used extensively include what are commonly known as gamma -rays, X-rays, andlor the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes.

As can be readily appreciated by one of ordinary skill in the art, the methods and pharmaceutical compositions of the present invention are particularly suited to administration to a mammal, preferable a human subject.

Intermediate endpoint biomarkers are measurable biologic alterations in tissue that occur between the initiation of and the development of frank neoplasia. It is hypothesized that modulation of one or more intermediate endpoint biomarkers by a chemopreventive agent may reflect true inhibition of carcinogenesis. A biomarker would be validated if the final endpoint, cancer incidence, were also reduced by the putative chemopreventive agent. Intermediate biomarkers in cancer may be classified into the following groups: histologic, proliferation, differentiation and biochemical markers. In any chemoprevention strategy, the availability of histologically recognizable and accepted precancerous lesions constitutes an important starting point. For the prostate, a possible histological marker is prostatic intraepithelial neoplasia (PIN), which is a precancerous precursor of prostatic adenocarcinoma. PIN appears as an abnormal proliferation within the prostatic ducts of premalignant foci of cellular dysplasia and carcinoma in situ without stromal invasion. PIN and histological prostate cancer are morphometrically and phenotypically similar. Thus, the development of high grade PIN may represent an important step in the progression pathway whereby the normal prostate develops PIN, histological prostate cancer, invasive clinical prostate cancer, and metastases.

The following examples are presented in order to more fully illustrate the preferred embodiments of the invention. They should in no way be construed, however, as limiting the broad scope of the invention.

EXPERIMENTAL DETAILS SECTION

Example 1: Transgenic Adenocarcinoma Mouse Prostate

The study of prostate cancer chemoprevention has been hindered by the lack of appropriate animal models. The recent development of the transgenic adenocarcinoma mouse prostate (TRAMP) model enables the study of chemoprevention. In the TRAMP model, which is described in Greenberg et al., "Prostate cancer in a transgenic mouse," Proc. Natl Acad. Sci. USA, 1995, Vol. 92, pages 3439–3443, the PB-SV40 large T antigen (PB-Tag) transgene is expressed specifically in the epithelial cells of the murine prostate. As a result, this model has several advantages over currently existing models: 1) mice develop progressive forms of prostatic epithelial hyperplasia as early as 10 weeks and invasive adenocarcinoma around 18 weeks of age; 2) the metastatic spread of prostate cancer pattern mimics human prostate cancer with the common sites of metastases being lymph node, lung, kidney, adrenal gland, and bone; 3) the development as well as the progression of prostate cancer can be followed within a relatively short period of 10–30 weeks; 4) the tumors arise with 100% frequency; and 5) the animals may be screened for the presence of the prostate cancer transgene prior to the onset of clinical prostate cancer to directly test treatment with chemopreventive agents that may alter prostate carcinogenesis.

The TRAMP transgenic mouse model is an excellent in vivo model to determine the mechanisms of initiation and promotion of prostate cancer and to test the effectiveness of potential chemopreventive agents. These mice progressively develop prostatic epithelial hyperplasia, PIN, and then prostate cancer within a short period (<17 weeks).

Chemopreventive treatment of hybrid TRAMP mice is initiated 30 days postnatally, using chemopreventive agents at a level of about 0.5–50 mg/kg of subject weight/day, preferably about 6–30 mg/kg of subject weight/day. The chemopreventive agents are conveniently processed into 21-day and 90-day pellets (prepared by Innovative Research of America, Sarasota, Fla.) and delivered as subcutaneous implants. Control animals receive placebo implants. In each drug treatment group, animals are sacrificed at 5, 7, 10, 15, 20, 25, 30, 40, and 50 weeks of age until the development of a palpable tumor. Blood is collected and pooled per treatment time point to evaluate changes in serum testosterone and estradiol. Prostatic tissues are harvested for morphometric, histologic, and molecular studies.

Figure 2:
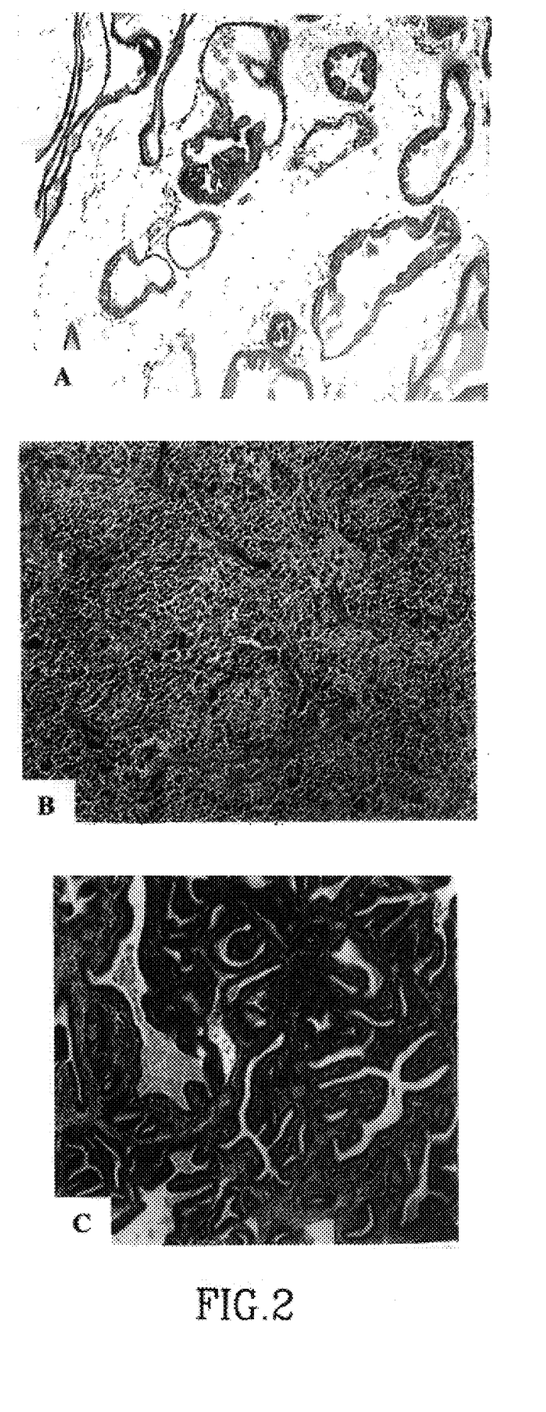
FIGS. 2A–2C: H&E sections illustrating ventral prostate cells in normal mice and prostate carcinoma in TRAMP mice included in the study.

The following test procedures are employed:
1) Prostate wholemount analysis is serially performed to detect changes in prostate ductal morphology over time with and without treatment; examples are shown in FIG. 2. Tissue sections are evaluated histologically by H&E and Masson-trichome standard staining. The emergence of PIN is assessed and graded (I-mild to III-severe).
2) Serum estradiol and total testosterone levels are measured (RIA) for 20 each age interval to assess any changes in these hormones as a result of chemopreventive agents.

Example 2: Immunohistochemistry Data Analysis

Microscopy images of each tissue section are evaluated by using computer-assisted (Mac 9500-I 132 computer and monitor) image quantitation (NIH-Image 1.6 PPC) using Kodak DCS 460 camera on Nikon Microphot-FX microscope and quantitated by using a color-assisted quantitative system image analysis (IPLab Spectrum 3.1, Scanalytics, Inc., VA) that discriminates color differences of stained tissue sections. Thresholds are set to identify various tissue components of the prostate. The area pixel densities corresponding to each of these tissue components are calculated for each full screen of the color monitor. A total of 5 screens per prostate section are averaged. Immunohistochemical images can be digitalized and quantitated to enable statistical evaluation by determination of sample correlation coefficients and probability (2-tailed).

Example 3: Study of Chemopreventive Activity

A study was undertaken to test the efficacy of chemopreventive agents in TRAMP transgenic animals (PBTag X FVBwt)(provided by Dr. Norman Greenberg, Baylor College of Medicine, TX). These mice showed preliminary signs of cancer as early as 10 weeks. The TRAMP transgenic male litters were screened for the Large T ag transgene, and the positive males were used in the study. The antiestrogen toremifene, which was to be tested for its possible chemopreventive effects, was incorporated in customized pellets (Innovative Research of America, Sarasota, Fla.), and chemopreventive treatment of mice was initiated postnatally at 30 days (average mouse weight 14g). Four groups of 10–12 animals each received subcutaneous implantations of 90 day-release to mifene-containing pellets. The diffusible drug dosage, adjusted for growth rated changes in weight, was designed to deliver either a low dose (6mg/kg) or a high dose (30mgIkg) of toremifene. Control animals (n=lO) received placebo implants. The efficacy of the treatment was measured by the absence of palpable tumor formation. The murine prostate tumors were harvested and evaluated by molecular and histological techniques.

Using the TRAMP transgenic model of prostate cancer, in which every animal that inherits the prostate cancer gene develops prostate cancer, it was demonstrated that toremifene both increases the latency and decreases the incidence of prostate cancer.

Figure 1:
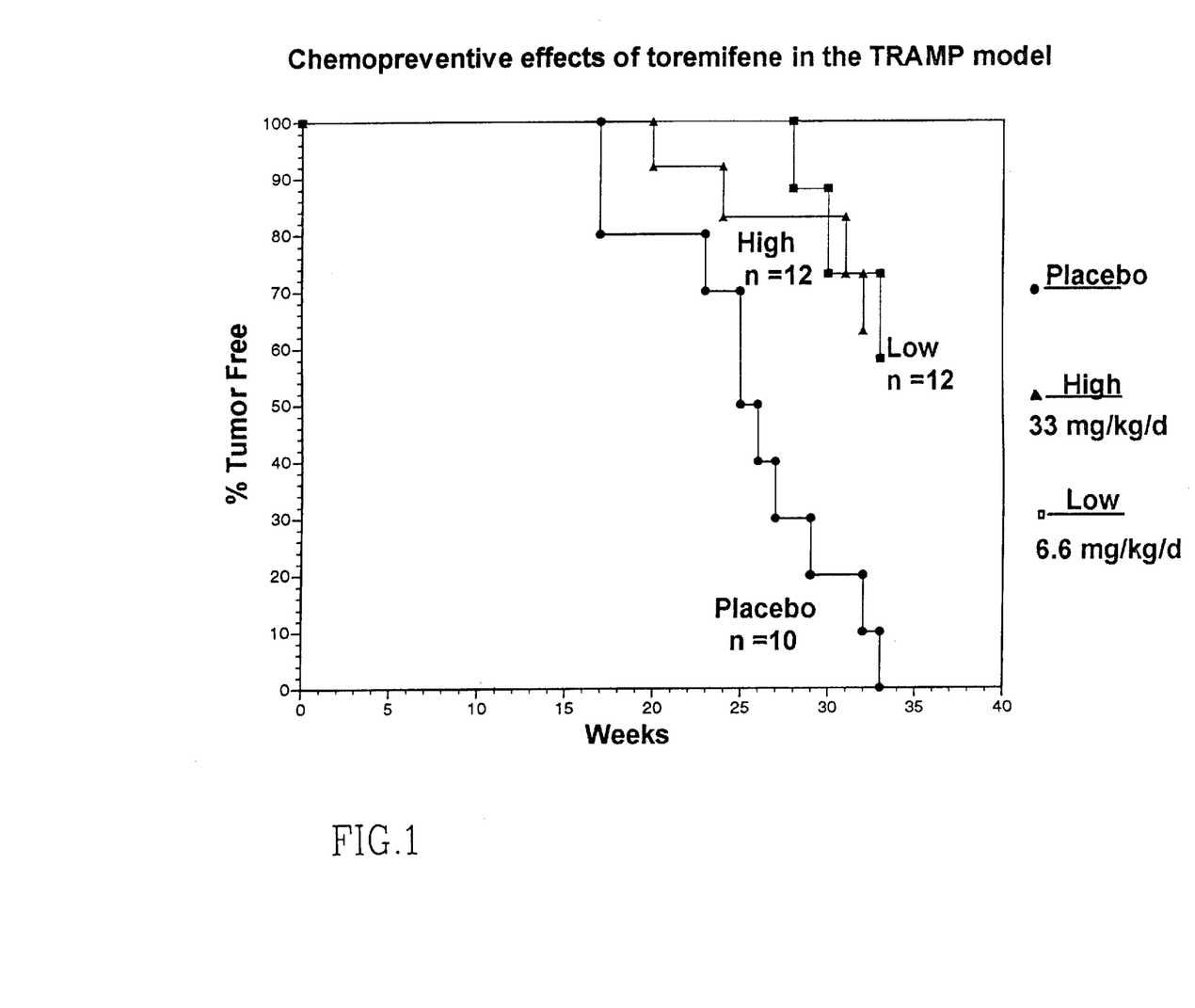
FIG. 1: A graph illustrating the chemopreventive effects of toremifene in the TRAMP model.

As shown in FIG. 1 the effects of low and high dose toremifene were both 30 effective. Tumor formation in the TRAMP mouse ventral prostate was noted at week 17 for the placebo group (n=lO), at week 19 for the high dose toremifene-treated group (n=12), and at week 28 for the low dose toremifene-treated group (n=12). Thus, 5 treatment by toremifene substantially increased the latency period by up to 11 weeks for the development of cancer in the ventral prostate of TRAMP mice.

Since the toremifene-treated animals did not reach the 50% tumor development point during the period of the study, the time in which 25% of the animals had tumors was compared among groups. Tumors were palpable in 25% of 10 the animals by week 23 in the placebo group and by 30–31 weeks in the high and low toremifene groups, a delay of 7–8 weeks. Both low toremifene and high toremifene vs placebo were significant by log rank and Wilcoxon statistical analysis, as shown in Table 1 below.

TABLE 1

| Statistical Analysis | | |
|---|---|---|
| | Log-Rank P | Wilcoxon p |
| Low toremifene vs placebo | 0.0003* | 0.0004* |
| High toremifene vs placebo | 0.0017* | 0.0071* |

*significance $P < 0.05$

At week 33, a point when all of the control animals had developed tumors, 72% of the low dose and 60% of the high dose toremifene-treated animals were still tumor-free. Thus, toremifene treatment at both low and high dosages resulted in a greatly decreased incidence of tumors in the ventral prostate of TRAMP mice.

These results, obtained in accordance with the present invention, would not have been predicted from those reported in the aforementioned paper of Lucia et al., which describes the administering at two dosage levels of tamoxifen, a close structural analog of toremifene, to Lobund-Wistar rats having prostate carcinomas induced by treatment with a combination of an initiator and a promoter. In the Lucia et al. reference, it is reported that only 22–26% of the animals receiving the lower dose and only 32–50% of those receiving the higher dose of tamoxifen remained free of tumors in the anterior prostate. It should be noted that the anterior prostate of a rodent, unlike its ventral prostate, has no corresponding segment in the prostate of a human subject.

In Lucia et al., it is further stated that the initiator-promoter combination employed in the described procedures, although effective in inducing cancer in the anterior prostate of the test animals, failed to induce carcinomas in the ventral prostate. Therefore there is no basis to expect a chemopreventive effect on tumors in the ventral prostate by administering tamoxifen to Lobund-Wistar rats or to humans.

As already discussed, administering toremifene produces a substantial chemopreventive effect against tumors in the ventral prostate of TRAMP mice. This result is encouraging for a similar beneficial effect on human subjects, whose prostate does include a segment corresponding to the ventral prostate of rodents.

Example 4: Histological Examination of Prostate Tissue

Tumors from the placebo and high toremifene- treated groups taken at the time of palpation were evaluated histologically. FIG. 2A is an H&E section of the ventral prostate of a 17-week-old normal adult mouse. FIG. 2B, a section of the ventral prostate of a placebo-treated 16-week-old TRAMP mouse, shows that, unlike the normal prostate structure depicted in FIG. 2A, the TRAMP mouse ventral prostate is characterized by sheets of undifferentiated, anaplastic cells with a high mitotic index. In contrast, as shown in FIG. 2C, the prostate of a toremifene-treated 30-week-old TRAMP mouse retains much of the normal glandular architecture and ha tumors with a more differentiated structure, the mitotic index being much lower than that for the placebo-treated animal. These results indicate that toremifene, even at low dosage, is able to suppress prostate carcinogenesis in the TRAMP model.

EXAMPLE 5: Use of Chemopreventive Efficacy of Toremifene Against Prostate Cancer in the TRAMP Mouse Model This experiment confirms and demonstrates the chemopreventive efficacy of toremifene. This present study focuses on the histological and molecular changes associated with development of prostate tumor in control animals and the mechanism of toremifene chemopreventive action with TRAMP animals which are bred, screened and treated with sustained-release drug pellets. At predetermined times, groups of 5 animals were sacrificed and their prostates were removed for analysis. The prostate glands were evaluated for the presence of tumor by histology, wholemount dissections, and large T antigen immunohistochemistry. To date, the Placebo and the Toremifene treatments have been completed for the 7, 10, 15 and 20 week time-points and the results are described below.

Figure 3:
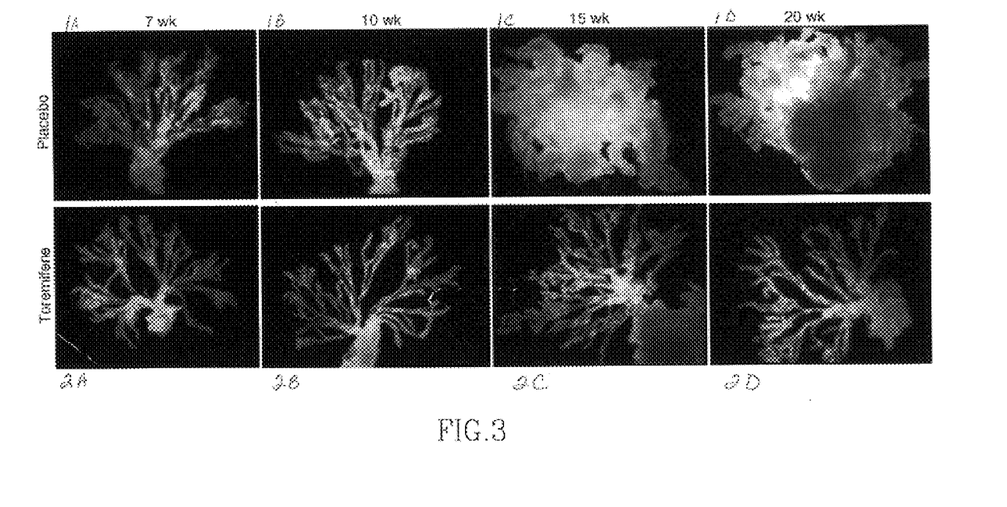
FIG. 3: Effect of Toremifene on ventral prostate development in the TRAMP mouse.
Figure 4:
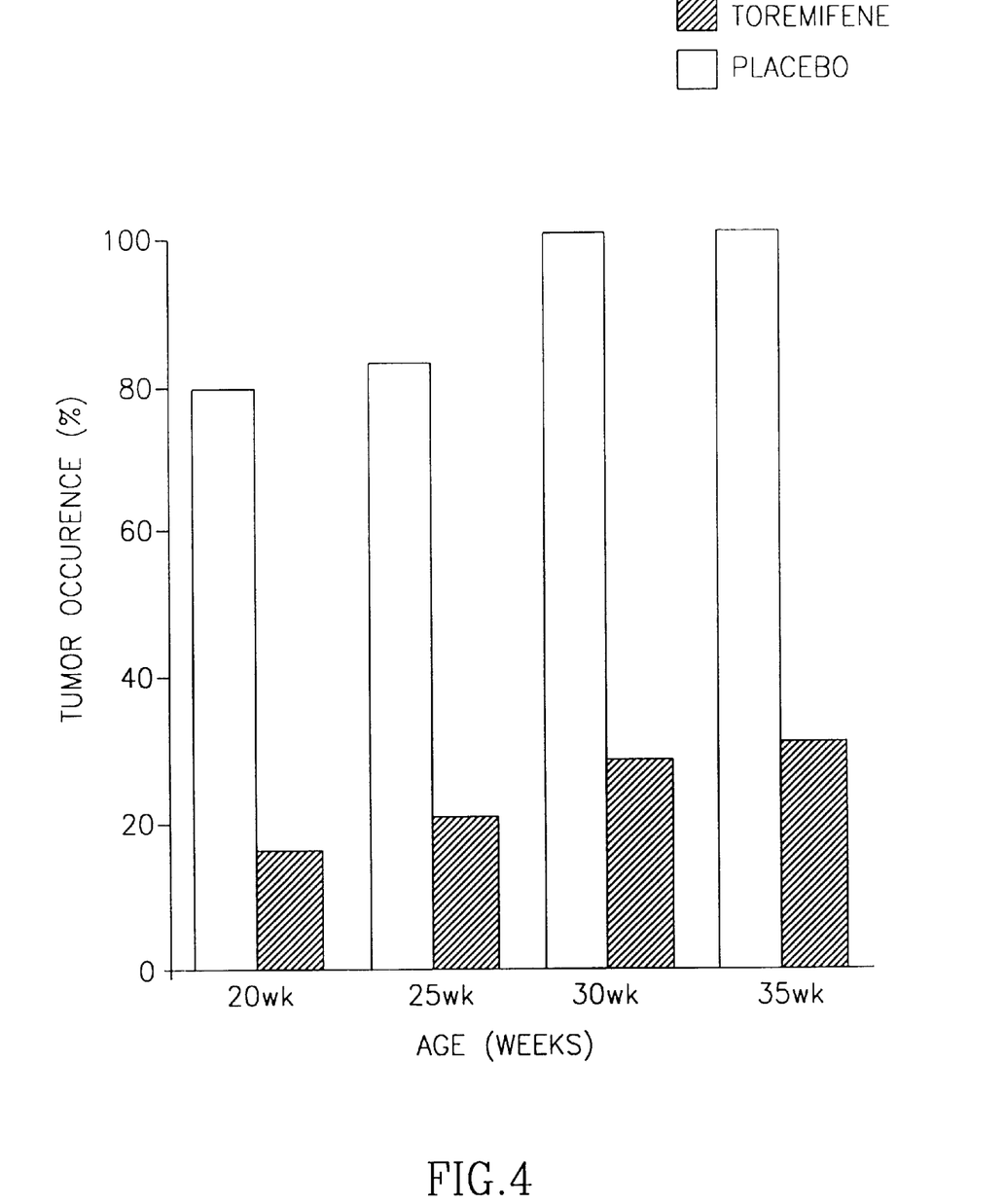
FIG. 4: Effect of Toremifene on tumor occurrence in the TRAMP mice.
Figure 5:
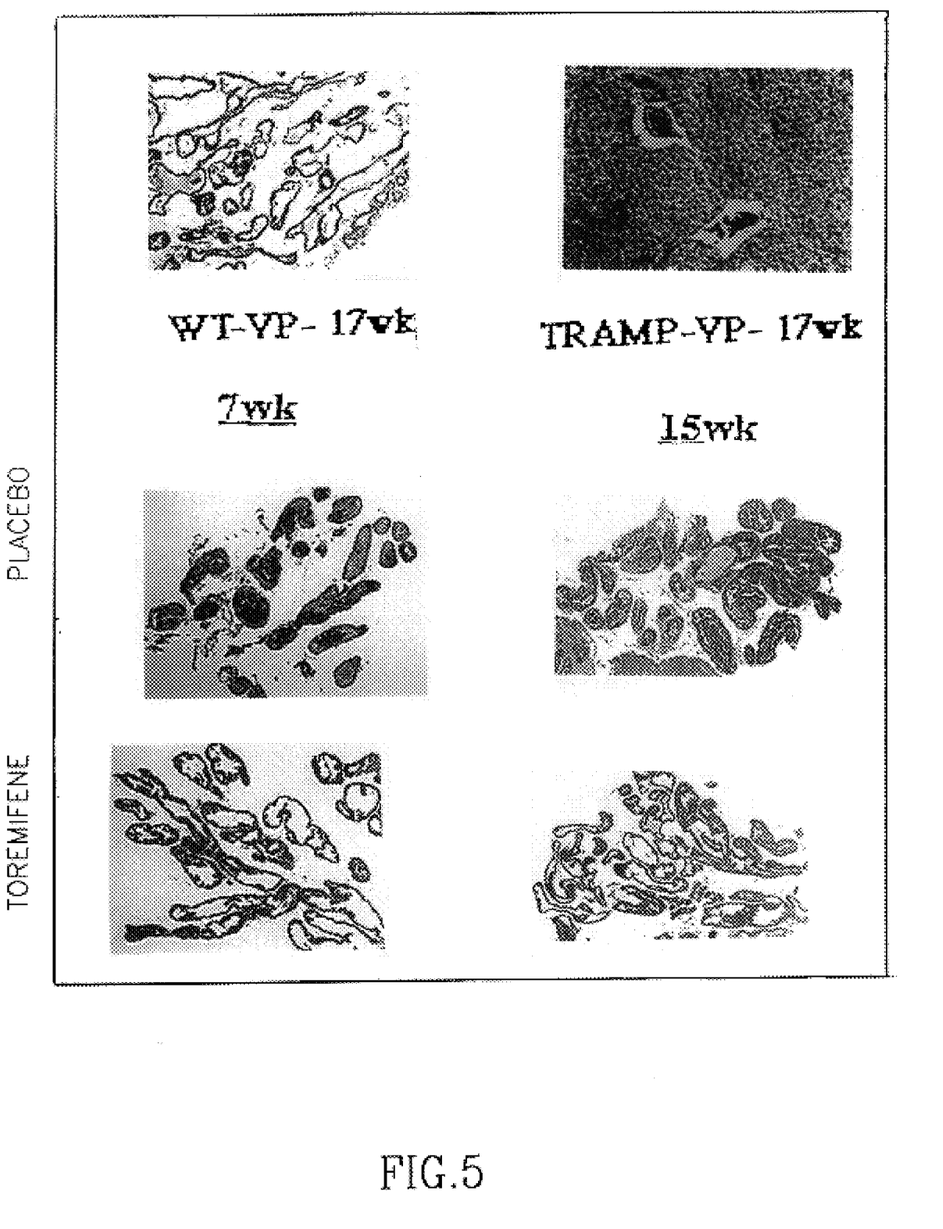
FIG. 5: Effect of Toremifene on tumor development in the TRAMP model.

Results: Prostaticwholemounts for 7, 10, 15, and 20 weeks forthe various groups have been completed. Whole-mount analysis revealed that placebo treated mice developed prostate tumors by 15–20 weeks of age similar to the previous pilot study. Moreover, the Toremifene treated animals had a delay in the occurrence of prostate cancer up to 20 weeks (FIG. 3). By 20 weeks, there is a striking delay in tumor occurrence in the Toremifene treated group up to 35 weeks FIG. 4). These data confirm that even with a more sensitive assessment of tumorigenicity, Toremifene exhibited chemopreventive activity. For histological evaluation, tissue samples were fixed, processed and paraffin embedded. Sections (5pM thick) were cut and stained by routine H&E method. Toremifene inhibited the ductal development and tissue differentiation (compare the 17 weeks TRAMP mouse prostate tumor vs. wildtype (FIG. 4); b) Toremifene treated prostate histology vs. Placebo at 15 weeks (FIG. 5) Qualitatively, immunohistochemistry of Placebo and Toremifene treated tissues showed presence of T-antigen in the ventral prostate. Thus, the chemopreventive activity seen by Toremifene does not appear to be by suppression of the probasin promoter in the TRAMP model.

Conclusions: The ability of Toremifene to prevent the occurrence of prostate cancer in the TRAMP model has been confirmed utilizing more sensitive techniques to assess tumor formation. The mechanism of Toremifene's chemopreventive effects does not appear to be through loss of the transgene for the Large T- antigen protein.

EXAMPLE 6: Toremifene Induces Regression of Established Human Prostate Cancer Tumors in the Nude Mouse Model Prostate cancer currently remains the most commonly diagnosed cancer in American males. However, questions remain about the etiology and treatment of this disease especially is advanced forms. Hormone therapy remains the standard method of treatment for recurrent and advanced prostate cancer despite the common development of hormone refractory disease. Therefore, new approaches for the prevention and treatment of prostate cancer are needed to accommodate the increasing number of men diagnosed with this disease. The experiments and results below demonstrate that toremifene suppresses hormone sensitive LNCaP tumor growth in athymic nude mice.

Materials and Methods: One million LNCaP cells in Matrigel were subcutaneously injected into each flank of athymic nude mice. A total 40 mice were injected. After approximately 3–4 weeks, visible tumors developed. After recording the tumor size in two dimensions, the mice were divided into placebo and treatment groups based on equivalent tumor burden. A single pellet (placebo versus toremifene 35 mg) was subcutaneously implanted between the scapulae of each mouse. Weekly measurements of the tumor size were recorded. Tumor volume was calculated (tumor volume=0.5(L+W)xLxWx 0.5236, where L=tumor length and W=width). The tumor volume at the time of pellet implantation served as the point of reference for future comparison of tumor's size variation. The weekly variations of each tumor volume were ded as percent differentiation from the original measurement at pellet tation.

Figure 6:
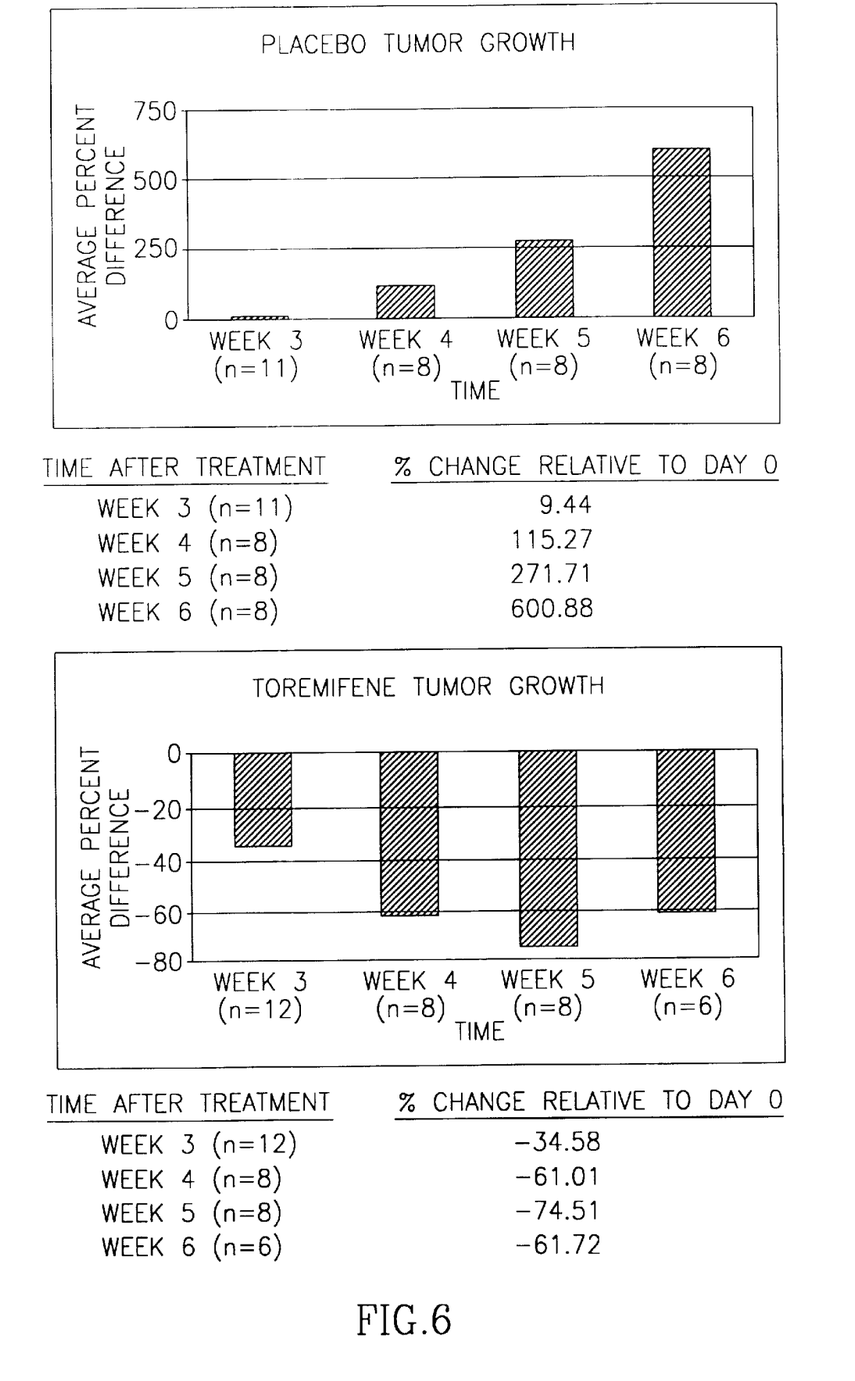

Results: Two mice died soon after pellet implantation due to mortal wounds from other mice. One mouse treated with toremifene was excluded from the study due excessive tumor hemorrhage and hematoma development. All mice developed visible tumors unilaterally or bilaterally. Each tumor was followed independently for the duration of the study. Twenty-four tumors were treated with placebo and 28 tumors were treated with toremifene. The results are shown in Table 2 and FIG. 6A and 6B.

TABLE 2

| Week | N= | % Change in volume relative to day 0 of treatment |
|---|---|---|
| | | PLACEBO GROUP |
| 3 | 11 | 9.44 |
| 4 | 8 | 115.27 |
| 5 | 8 | 271.71 |
| 6 | 8 | 600.88 |
| | | TOREMIFENE |
| 3 | 11 | −34.58 |
| 4 | 7 | −61.01 |
| 5 | 7 | −74.51 |
| 6 | 5 | −61.72 |

The follow-up interval will be extended on the currently reported population and data on additional animals are presently being collected.

Conclusion: Toremifene inhibits and induces regression of established LNCaP tumors. Although the mechanism by which toremifene exerts this effect is unknown, the ability to produce these effects supports the use of Toremifene as a treatment for prostate cancer and to prevent the recurrence of prostate cancer in high risk patients with established prostate cancer micrometastases.

What is claimed is:

1. A method for preventing prostate carcinogenesis comprising: administering to a mammalian subject having precancerours precursors of prostate adenocarcinoma and not having prostate cancer, a pharmaceutical preparation comprising a chemopreventive agent having the formula:

(1)

wherein $R_1$ and $R_2$, which can be the same or different, are H or OH; $R_3$ is $OCH_2CH_2NR_4R_5$, wherein $R_4$ and $R_5$, which can be the same or different, are H or an alkyl group of 1 to about 4 carbon atoms;

and their pharmaceutically acceptable salts, esters, or N-oxides, and mixtures thereof.

2. The method according to claim 1, wherein said pharmaceutical preparation further comprises a pharmaceutically acceptable carrier.

3. The method according to claim 2, wherein said carrier is selected from the group consisting of a gum, a starch, a sugar, a cellulosic material, and mixtures thereof.

4. The method according to claim 1, wherein said administering comprises: subcutaneously implanting in said subject a pellet containing said pharmaceutical preparation.

5. The method according to claim 4, wherein said pellet provides for controlled release of said pharmaceutical preparation over a period of time.

6. The method according to claim 1, wherein said administering intravenously, intraarterially, or intramuscularly injecting in said subject said pharmaceutical preparation in liquid form.

7. The method according to claim 1, wherein said administering orally administering to said subject a liquid or solid preparation containing said pharmaceutical preparation.

8. The method according to claim 1, wherein said administering topically applying to skin surface of said subject said pharmaceutical preparation.

9. The method according to claim 1, wherein said pharmaceutical preparation is selected from the group consisting of a pellet, a tablet, a capsule, a solution, a suspension, an emulsion, an elixir, a gel, a cream, and a suppository.

10. The method according to claim 9, wherein said suppository is a rectal suppository or a urethral suppository.

11. The method according to claim 1, wherein said pharmaceutical preparation is a parenteral formulation.

12. The method according to claim 11, wherein said parenteral formulation comprises a liposome comprising a complex of said chemopreventive agent and a cyclodextrin compound.

13. The method according to claim 1, wherein said chemopreventive agent comprises toremifene, its N-oxide, pharmaceutically acceptable salts, and mixtures thereof.

14. The method according to claim 1, wherein said administering is carried out at a dosage of about 0.5 mg/kg of subject weight/day to about 50 mg/kg of subject weight/day of said chemopreventive agent.

15. The method according to claim 14, wherein said administering is carried out at about 6 mg/kg of subject weight/day to about 30 mg/kg of subject weight/day of said chemopreventive agent.

16. The method of claim 1, wherein the precancerous precursors of prostate adenocarcinoma is prostate intraepithelial neoplasia (PIN).

17. A method for preventing prostate carcinogenesis comprising: administering to a mammalian subject having precancerous precursors of prostate adenocarcinoma and not having prostate cancer a composition comprising a chemopreventive agent having the formula:

(1)

wherein $R_1$ and $R_2$, which can be the same or different, are H or OH; $R_3$ is $OCH_2CH_2NR_4R_5$, wherein $R_4$ and $R_5$, which can be the same or different, are H or an all group of 1 to about 4 carbon atoms.

18. The method according to claim 17, wherein said composition further comprises an acceptable carrier.

19. The method of claim 18, wherein the precancerous precursors of prostate adenocarcinoma is prostate intraepithelial neoplasia (PIN).

* * * * *